(12) United States Patent
Dafinger et al.

(10) Patent No.: US 10,947,178 B2
(45) Date of Patent: Mar. 16, 2021

(54) METHOD FOR PRODUCING VINYL ACETATE

(71) Applicant: WACKER CHEMIE AG, Munich (DE)

(72) Inventors: Willibald Dafinger, Roehrnbach (DE); Brigitte Patsch, Burghausen (DE); Guenther Rudolf, Muehldorf (DE)

(73) Assignee: WACKER CHEMIE AG, Munich (DE)

(*) Notice: Subject to any disclaimer, the term of this patent is extended or adjusted under 35 U.S.C. 154(b) by 0 days.

(21) Appl. No.: 16/760,306

(22) PCT Filed: Nov. 21, 2017

(86) PCT No.: PCT/EP2017/079933
§ 371 (c)(1),
(2) Date: Apr. 29, 2020

(87) PCT Pub. No.: WO2019/101296
PCT Pub. Date: May 31, 2019

(65) Prior Publication Data
US 2020/0277249 A1    Sep. 3, 2020

(51) Int. Cl.
*C07C 67/05* (2006.01)
*C07C 69/15* (2006.01)
*C07C 67/055* (2006.01)

(52) U.S. Cl.
CPC ............ *C07C 67/055* (2013.01); *C07C 69/15* (2013.01); *C07C 2523/44* (2013.01)

(58) Field of Classification Search
CPC .............................. C07C 67/055; C07C 67/05
See application file for complete search history.

(56) References Cited

U.S. PATENT DOCUMENTS

| 9,561,997 B2 * | 2/2017 | Dafinger ................. C07C 67/04 |
| 2006/0094896 A1 | 5/2006 | Rinne et al. |
| 2011/0054210 A1 | 3/2011 | Westermayer et al. |
| 2016/0311752 A1 | 10/2016 | Dafinger et al. |

FOREIGN PATENT DOCUMENTS

| EP | 1655279 B1 | 2/2017 |
| KR | 1020080097529 A | 11/2008 |
| WO | 2009130211 A1 | 10/2009 |
| WO | 2010149527 A1 | 12/2010 |
| WO | 2012058196 A1 | 5/2012 |
| WO | 2015082450 A1 | 6/2015 |

\* cited by examiner

*Primary Examiner* — Paul A Zucker
(74) *Attorney, Agent, or Firm* — Brooks Kushman P.C.

(57) ABSTRACT

Fouling of the acetic acid saturator by recycle gas in the continuous gas phase process for manufacture of vinyl acetate is reduced by adding an N-oxyl fouling inhibitor to the saturator and/or at one or more other addition sites in the process, in amounts such that the concentration of N-oxyl compound which accumulates in the saturator bottoms is from 10 to 100 ppm. The amount of N-oxyl compound in the saturator is preferably from 10-50 ppm. The reduction in fouling is evidenced by lessening the lowering of the heat transfer coefficient of the saturator over time.

5 Claims, 1 Drawing Sheet

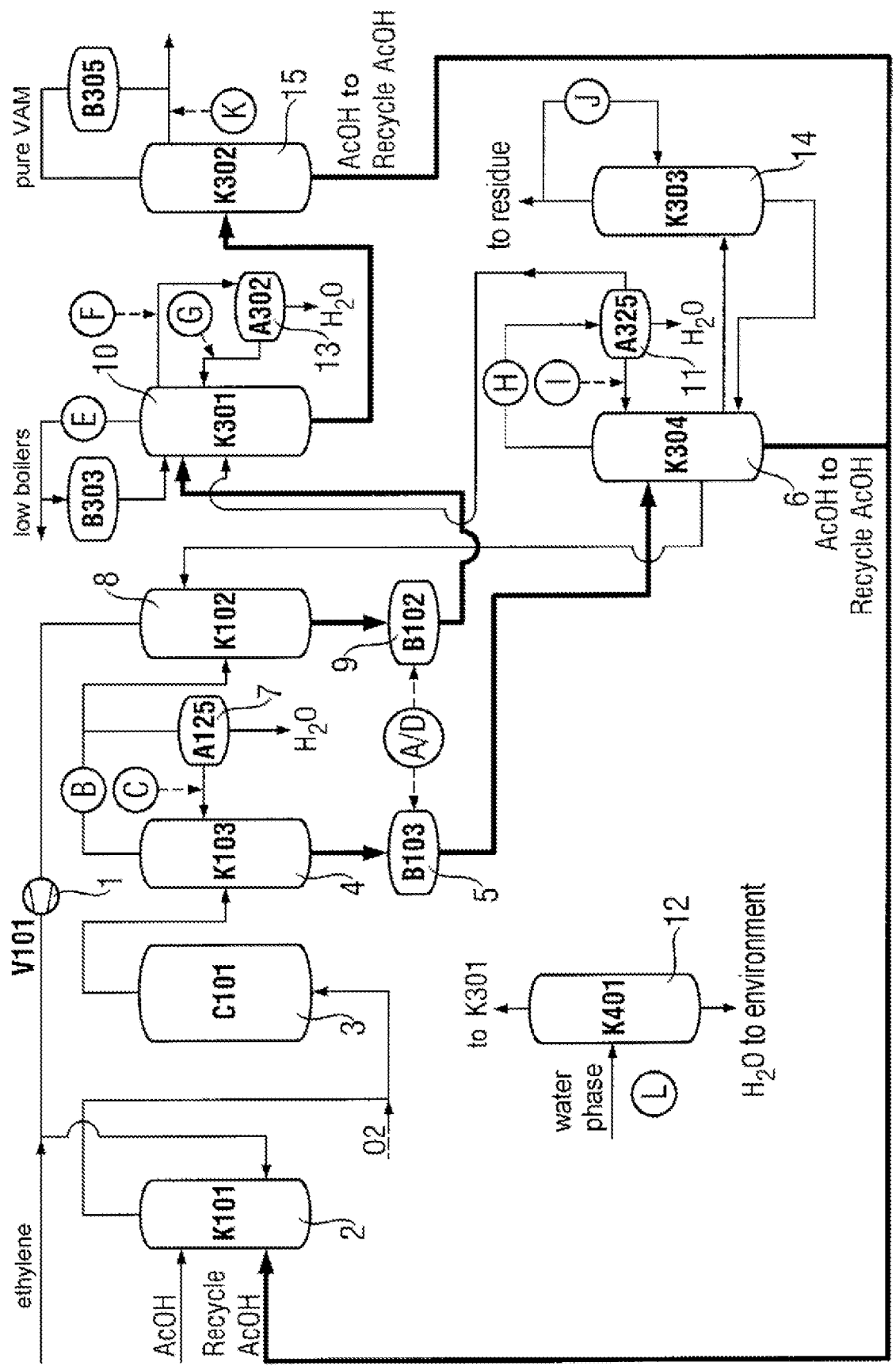

METHOD FOR PRODUCING VINYL ACETATE

CROSS REFERENCE TO RELATED APPLICATIONS

This application is the U.S. National Phase of PCT Appln. No. PCT/EP2017/079933 filed Nov. 21, 2017, the disclosure of which is incorporated in its entirety by reference herein.

BACKGROUND OF THE INVENTION

1. Field of the Invention

The invention relates to a process for producing vinyl acetate in a heterogeneously catalyzed, continuous gas phase process via reaction of ethylene with acetic acid and oxygen in a fixed bed tubular reactor and workup of the product gas stream, wherein a gas mixture consisting predominantly of ethylene, carbon dioxide, ethane, nitrogen and oxygen (=cycle gas) is circulated, and the cycle gas is admixed with the reactants acetic acid, ethylene and oxygen upstream of the fixed bed tubular reactor and is brought to reaction temperature by means of heat exchangers operated with heating steam, and wherein the enrichment of the cycle gas with acetic acid is effected in an acetic acid saturator.

2. Description of the Related Art

Vinyl acetate monomer (VAM) can be produced in a continuous process in which the purified product stream is recycled (cycle gas process). Here, in a heterogeneously catalyzed gas phase reaction, ethylene reacts with acetic acid and oxygen on catalysts which generally contain palladium salts and alkali metal salts on a support material and may additionally also have been doped with gold or rhodium. Preference is given to using a Pd/Au catalyst mixture with a potassium acetate promoter.

The reactants ethylene, oxygen and acetic acid are reacted in an exothermic reaction (VAM: $\Delta_B H°_{299}$=−176 kJ/mol), in general at a positive pressure of 7 to 15 bar and, depending on the lifetime of the catalyst, at a temperature of in general from 130° C. to 200° C., in a fixed bed tubular reactor, but also fluidized bed reactors, to give vinyl acetate:

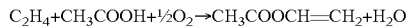

$$C_2H_4+CH_3COOH+\tfrac{1}{2}O_2 \rightarrow CH_3COOCH=CH_2+H_2O$$

The principal side reaction here is the total oxidation of ethylene to $CO_2$: $C_2H_4+3\ O_2 \rightarrow 2\ CO_2+2\ H_2O$ ($CO_2$: $\Delta_B H°_{299}$=−1322 kJ/mol)

Ethylene conversion is generally about 5% to 20%, acetic acid conversion 20% to 60%, and oxygen conversion up to 90%.

Because of the incomplete conversion of ethylene, a gas mixture consisting predominantly of ethylene, carbon dioxide, ethane, nitrogen, and oxygen (=cycle gas) is circulated during the production of vinyl acetate. The cycle gas is admixed with the reactants acetic acid, ethylene and oxygen upstream of the fixed-bed tubular reactor and brought to reaction temperature by means of heat exchangers operated with heating steam. Enrichment of the cycle gas with acetic acid is usually effected using an acetic acid saturator heated with heating steam.

However, the loading of cycle gas with acetic acid in the acetic acid saturator has the drawback that the acetic acid saturator becomes fouled even after short run times. The saturator is generally a column in which dry cycle gas (without acetic acid or water) is firstly passed directly into the column from the bottom up and acetic acid is metered in. Especially in the lower column region, there is fouling at the point of introduction of the dry and hot cycle gas, which impairs the production capacity and even triggers a shutdown of production for cleaning.

WO 2009/130211 A1 describes that the fouling in the acetic acid saturator can be reduced by means of presaturation of the cycle gas with returned acetic acid in a presaturator connected upstream of the acetic acid saturator.

EP 1 655 279 B1 describes a process for the saturation of the cycle gas with acetic acid in an acetic acid saturator, where the liquid withdrawn from the acetic acid saturator is divided into two substreams and one substream is recycled into the acetic acid saturator while maintaining a minimum pumped circulation. This process is purported to circumvent the fouling problem in the acetic acid saturator.

It was an object of the invention to make available a process with which the fouling of the acetic acid saturator can be effectively prevented without the apparatus mentioned.

It was known from the prior art that, when working up the product gas mixture from the gas phase oxidation, the fouling of the columns used in the process can be prevented by adding compounds having at least one N-oxyl radical group —N—O.. KR 10-2008-97529 describes the addition of 2,2,6,6-tetramethylpiperidinyloxyl (TEMPO) or of 4-oxo-TEMPO when working up the cycle gas. WO 2010/149527 A1 describes the addition of TEMPO or OH-TEMPO when working up the VAM-containing product gas stream. In WO 2015/082450 A1, the N-oxyl compound is used to this end in the form of an aqueous solution. WO 2012/058196 A1 describes the addition of free-radical scavengers for the treatment of the product gas stream from the gas phase oxidation of ethylene and acetic acid to vinyl acetate.

SUMMARY OF THE INVENTION

The invention provides a process for producing vinyl acetate in a heterogeneously catalyzed, continuous gas phase process via reaction of ethylene with acetic acid and oxygen in a fixed bed tubular reactor and workup of the product gas stream, wherein a gas mixture consisting predominantly of ethylene, carbon dioxide, ethane, nitrogen and oxygen (=cycle gas) is circulated, and the cycle gas is admixed with the reactants acetic acid, ethylene and oxygen upstream of the fixed bed tubular reactor and is brought to reaction temperature by means of heat exchangers operated with heating steam, and wherein the enrichment of the cycle gas with acetic acid is effected in an acetic acid saturator, characterized in that one or more N-oxyl compounds containing at least one N-oxyl radical group —N—O, from the group comprising 2,2,6,6-tetramethylpiperidinyloxyl, 4-hydroxy-2,2,6,6-tetramethylpiperidinyloxyl, 4-oxo-2,2,6,6-tetramethylpiperidinyloxyl and 4-ethanoyloxy-2,2,6,6-tetramethylpiperidinyloxyl, is added to the acetic acid saturator in such an amount that the concentration of the N-oxyl compound in the column bottoms of the acetic acid saturator is 10 to 100 ppm by weight, based on the weight of the column bottoms of the acetic acid saturator.

BRIEF DESCRIPTION OF THE DRAWINGS

The drawing FIGURE gives a simplified scheme for the production of vinyl acetate in a gas phase process and subsequent workup of the product gas stream.

DETAILED DESCRIPTION OF THE PREFERRED EMBODIMENTS

Preferred N-oxyl compounds are those based on secondary amines in which the N-oxyl group is part of a saturated or unsaturated six-membered ring, for example piperidin-1-oxyl compounds, and in which the carbon atoms adjacent to the N-oxyl group each bear two $C_1$- to $C_4$-alkyl groups, preferably methyl groups. 2,2,6,6,-tetramethylpiperidinyloxyl (TEMPO) and 4-hydroxy-2,2,6,6,-tetramethylpiperidinyloxyl (4-OH-TEMPO) are preferred.

The N-oxyl compound is generally metered in as a solution. Suitable solvents are vinyl acetate, vinyl acetate-water mixtures or water. Preference is given to using, as solvent, vinyl acetate or a vinyl acetate-water mixture. The N-oxyl compound is most preferably added in the form of a 5% to 10% by weight solution in a vinyl acetate-water mixture.

The amount of N-oxyl compound required for the process firstly depends on the construction and capacity of the respective plant. In general, 200 to 500 ppm by weight, preferably 200 to 400 ppm by weight, of N-oxyl compound is fed, in each case based on one metric ton of vinyl acetate in the product gas stream.

The N-oxyl compound can be fed to the acetic acid saturator K-101 (2) as a constituent of the fresh acetic acid (FIG. 1: AcOH) or as a constituent of the recycle acetic acid (FIG. 1: recycle AcOH) or both with the fresh acetic acid and with the recycle acetic acid.

The N-oxyl compound is added in such an amount that the concentration of the N-oxyl compound in the column bottoms of the acetic acid saturator is 10 to 100 ppm by weight, preferably 10 to 50 ppm by weight.

Particular preference is given to an embodiment in which the N-oxyl compound is added at one or more points, labelled as points A to K in FIG. 1, during the workup of the product gas stream and is added there in such an amount that, via the feed as a constituent of the recycle acetic acid, a concentration of the N-oxyl compound in the column bottoms of the acetic acid saturator of 10 to 100 ppm by weight, preferably 10 to 50 ppm by weight, is established.

With reference to FIG. 1, the cycle gas that has been compressed by the cycle gas compressor V-101 (1) is enriched with fresh ethylene, which replaces the portion of ethylene consumed in the reaction, and is fed to the acetic acid saturator K-101 (2). The acetic acid converted in the reaction is replaced in the acetic acid saturator K-101 (2) by feeding in fresh acetic acid and recycle acetic acid. The high boilers and other by-products, such as for example all recycled polymers and unconsumed inhibitors, are taken off at the bottom of the acetic acid saturator (2), freed from residual acetic acid in the acetic acid workup and the remaining residues are disposed of.

Since complete conversion of the acetic acid does not take place in the reaction, in the following distillations (for example in the azeotrope column K-304 (6) and the pure VAM column K-302 (15)) this acetic acid is taken off at the bottom of the respective column and fed to the recycle acetic acid tank.

Prior to entry into the reactor system, oxygen is added via a nozzle to the cycle gas leaving the acetic acid saturator K-101 (2) and loaded with acetic acid. Next, the cycle gas is fed at a cycle gas pressure of 7 to 15 bar abs. to the fixed bed tubular reactor C-101 (3) which is charged with a Pd/Au catalyst mixture with potassium acetate promoter and is operated at a temperature of 130 to 200° C.

The gas stream leaving the fixed bed tubular reactor C-101 (3) is fed to the lower portion of the preliminary dewatering column K-103 (4). A first condensate (vinyl acetate, water and unreacted acetic acid) from this column is passed into the crude VAM vessel B-103 (5). The crude VAM vessel B-103 (5) is point A, at which the N-oxyl compound can be added.

The crude VAM from the crude VAM vessel B-103 (5) is thereafter pumped into the azeotrope column K-304 (6). The main gas stream from the preliminary dewatering column K-103 (4) can be admixed with the N-oxyl compound upstream of the subsequent condensation in the cycle gas scrubber K-102 (8) (point B). To inhibit the return stream from the phase separator A-125 (7), the N-oxyl compound can be added on the way to the preliminary dewatering column K-103 (4) (point C).

The uncondensed component of the top vapors of the preliminary dewatering column (4), essentially ethylene, $CO_2$ and vinyl acetate, is delivered to the cycle gas scrubber K-102 (8). The uncondensed VAM portions are absorbed in the acetic acid-operated cycle gas scrubber K-102 (8). The absorption AcOH required for the cycle gas scrubbing can be fed from the azeotrope column K-304 (6). The now VAM-free cycle gas is fed back to the reaction in reactor C-101 (3) via the cycle gas compressor V-101 (1) and the acetic acid saturator K-101 (2). The bottom product from the cycle gas scrubber K-102 (8) is passed into the crude VAM vessel B-102 (9) and from there into the dewatering column K-301 (10). N-oxyl compound can also be added in the crude VAM vessel B-102 (9) and/or in the crude VAM vessel B-103 (5) (point D).

Preferably, a second crude VAM stream is further generally passed into the dewatering column K-301 (10): the crude VAM from the crude VAM vessel B-103 (5) (=condensate from preliminary dewatering (4)). This is initially distilled in the azeotrope column K-304 (6). The top product of this distillation in the azeotrope column K-304 (6), essentially vinyl acetate and water, is transferred into the phase separator A-325 (11) for the removal of water, and can be admixed with the N-oxyl compound between the azeotrope column (6) and the phase separator (11) (point H).

The majority of the organic phase (essentially VAM) from the phase separator A-325 (11) is pumped back into the azeotrope column K-304 (6) as return stream and can be admixed beforehand with the N-oxyl compound (point I). The remaining portion of the organic phase is transferred to the dewatering column K-301 (10).

The aqueous phase of the phase separator A-325 (11) is conveyed to the waste water column K-401 (12) in which all aqueous phases from the phase separators A-125 (7), phase separator A-302 (13) and phase separator A-325 (11) of the entire distillation process are worked up. The aqueous bottom product of the waste water column (12) is disposed of, and the top product is recycled into the dewatering column K-301 (10).

For removal of the ethyl acetate, a side draw of the azeotrope column K-304 (6) can be passed to the ethyl acetate column K-303 (14). N-oxyl compound can likewise be metered into the return stream of this ethyl acetate column K-303 (14) (point J).

Preferably, in the dewatering column K-301 (10) essentially the bottom product from the cycle gas scrubber K-102 (8), which essentially contains water, vinyl acetate, acetic acid and low boilers (especially acetaldehyde), is separated: the low boilers and water are removed from vinyl acetate and acetic acid. This involves removing the acetaldehyde formed here by vinyl acetate hydrolysis via the top of the dewatering column K-301 (10), subsequently condensing it and pumping it for further workup. An N-oxyl compound can also be added at this point (point E).

The aqueous side draw can be passed to the phase separator A-302 (13) via an intermediate tray of the dewatering column K-301 (10). N-oxyl compound can be added to this line (point F). The organic phase is optionally likewise admixed with the N-oxyl compound (point G) and then, optionally at more than one point, is fed back as return stream to the dewatering column K-301 (10).

The bottom product of the dewatering column K-301 (10), vinyl acetate and acetic acid, is passed to the pure VAM column K-302 (15). Pure VAM is removed via the top and partly recycled as return stream. The N-oxyl compound can also be added to this return stream (point K). The bottom product, essentially acetic acid, is fed to the acetic acid workup.

In a particularly preferred embodiment, the N-oxyl compound is added to at least one of the columns from the group of azeotrope column K-304 (6), dewatering column K-301 (10), pure VAM column K-302 (15). In FIG. 1, the route of the N-oxyl compound to the acetic acid saturator when added to these columns has been marked with a bold line.

The $CO_2$ scrubbing and the acetic acid workup are not described in this scheme in FIG. 1.

The procedure according to the invention not only markedly reduces the polymer formation rates in the columns for working up the product gas stream and hence also the fouling, but also markedly reduces the fouling in the acetic acid saturator system. This is achieved by overdosing when adding to the columns, via one or more of the points A to K, that is to say that more N-oxyl compound is added than is respectively necessary for inhibition of the fouling at these points, and excess and unreacted N-oxyl compound consequently reaches the acetic acid saturator system via the recycle acetic acid. The time intervals between cleaning operations of the columns or filter changes are extended, plant availability is increased and hence the VAM yield is improved. Last but not least, the effective reduction in fouling in the acetic acid saturator makes a significant contribution to increasing operational reliability.

The following examples serve to further elucidate the invention:

Example 1

In a plant as per FIG. 1, which was operated under the abovementioned conditions (cycle gas pressure 7 to 15 bar abs., reaction temperature 130 to 200° C.) with a gas hourly space velocity (GHSV) of approx. 3000 to 4000 [1/h] and a space-time yield (STY) of 600 to 1200 (kg VAM/m³ cat. x h), 200 to 400 ppm by weight of 4-hydroxy-2,2,6,6,-tetramethylpiperidin-1-oxyl (4-OH-TEMPO), in each case as a solution in a vinyl acetate-water mixture, was added at each of the points A to L, so that the 4-OH-TEMPO was present in the bottoms of the acetic acid saturator K-101 (2) in an amount of 10 to 50 ppm by weight.

To assess the fouling of the acetic acid saturator K-101 (2), the heat transfer coefficient k in W/(m² K) was determined over a period of 7 months. The greater the fouling at the acetic acid saturator, the lower the heat transfer at the acetic acid saturator and the smaller the value k.

The heat transfer coefficient k at the start of the series of measurements was 750 W/(m² K) and after seven months was 650 W/(m² K).

Comparative Example 2

The procedure was analogous to example 1, with the difference that only 100 to 200 ppm by weight of 4-hydroxy-2,2,6,6,-tetramethylpiperidin-1-oxyl (4-OH-TEMPO), in each case as a solution in a vinyl acetate-water mixture, was added at each of the points A to L, and no 4-OH-TEMPO reached the acetic acid saturator K-101 (2).

The heat transfer coefficient k at the start of the series of measurements was 750 W/(m² K) and after seven months was 300 W/(m² K).

Whereas in the procedure according to the invention (example 1) the k value only decreased by 13% over a run time of 7 months, the k value without the measure according to the invention (comparative example 2) lost 80% of its value within 7 months.

The invention claimed is:

1. A process for producing vinyl acetate in a heterogeneously catalyzed, continuous gas phase process via reaction of ethylene with acetic acid and oxygen in a fixed bed tubular reactor and workup of the product gas stream, wherein a cycle gas mixture consisting predominantly of ethylene, carbon dioxide, ethane, nitrogen and oxygen is circulated, and the cycle gas is admixed with the reactants acetic acid, ethylene and oxygen upstream of the fixed bed tubular reactor and is brought to reaction temperature by means of heat exchangers operated with heating steam, and wherein the enrichment of the cycle gas with acetic acid is effected in an acetic acid saturator containing bottoms, the improvement comprising:
adding one or more N-oxyl compounds containing at least one N-oxyl radical group —N—O., selected from the group consisting of 2,2,6,6-tetramethylpiperidinyloxyl, 4-hydroxy-2,2,6,6-tetramethylpiperidinyloxyl, 4-oxo-2,2,6,6-tetramethylpiperidinyloxyl and 4-ethanoyloxy-2,2,6,6-tetramethylpiperidinyloxyl, to the acetic acid saturator in an amount such that the concentration of the N-oxyl compound in the bottoms of the acetic acid saturator is 10 to 100 ppm by weight, based on the weight of the bottoms of the acetic acid saturator.

2. The process of claim 1, wherein the N-oxyl compound is added to at least one of a fresh acetic acid stream and/or to a recycle acetic acid stream fed to the acetic acid saturator.

3. The process of claim 1, wherein the N-oxyl compound is added at one or more points during the workup of the product gas stream, in amounts such that the N-oxyl compound enters the acetic acid saturator as a constituent of a recycle acetic acid stream.

4. The process as claimed in claim 3, wherein one or more of a preliminary dewatering column, a cycle gas scrubber, an azeotrope column, an ethyl acetate column, a dewatering column and a pure vinyl acetate column is/are present, and wherein the N-oxyl compound during the workup of the product gas stream is added to one or more of:
a condensate from the preliminary dewatering column,
a gas stream from the preliminary dewatering column,
a return stream to the preliminary dewatering column,
a bottom product from the cycle gas scrubber,
a top product of the azeotrope column,
a return stream into the azeotrope column,
a return stream into the ethyl acetate column,
a top product of the dewatering column,
a side draw of the dewatering column,
a return stream into the dewatering column, or
a top product of the pure vinyl acetate column.

5. The process of claim 1, wherein the N-oxyl compound is added in such an amount that the concentration of the N-oxyl compound in the bottoms portion of the acetic acid saturator is 10 to 50 ppm by weight.

* * * * *